United States Patent [19]

Furukawa et al.

[11] 4,052,391
[45] Oct. 4, 1977

[54] 3-(DISUBSTITUTED)AMINOISO-THIAZOLO[3,4-d]PYRIMIDINES

[75] Inventors: Yoshiyasu Furukawa; Osamu Miyashita, both of Osaka, Japan

[73] Assignee: Takeda Chemical Industries, Ltd., Osaka, Japan

[21] Appl. No.: 663,227

[22] Filed: Mar. 3, 1976

Related U.S. Application Data

[62] Division of Ser. No. 522,863, Nov. 11, 1974, Pat. No. 3,959,280.

[30] Foreign Application Priority Data

Nov. 12, 1973    Japan ............................. 48-127050

[51] Int. Cl.$^2$ ........................................ C07D 513/04
[52] U.S. Cl. ......... 544/117; 260/256.5 R; 424/248.51; 424/251
[58] Field of Search .................. 260/256.5 R, 247.1 L

[56] References Cited

U.S. PATENT DOCUMENTS

| 3,674,786 | 7/1972 | Rajappa | 260/247.1 |
| 3,959,280 | 5/1976 | Furukawa et al. | 260/256.5 R |

Primary Examiner—Leonard Schenkman
Attorney, Agent, or Firm—Wenderoth, Lind & Ponack

[57] ABSTRACT

Novel 3-(disubstituted)aminoisothiazolo[3,4-d]pyrimidines of the formula

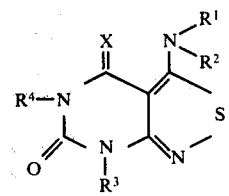

wherein $R^1$, $R^2$ and $R^3$ are respectively alkyl, alkenyl, aryl, aralkyl or aralkenyl, each of which may be substituted, or $R^1$ and $R^2$ form together with the adjacent nitrogen a heterocyclic ring which may be substituted, $R^4$ is hydrogen or alkyl and X is oxygen or imino with a proviso that when X is imino $R^4$ is hydrogen, show an eminent adenosine-3',5'-cyclic phosphate phosphodiesterase-inhibitory activity, and exhibit excellent pharmacological actions such as anti-inflammatory and sedative activities.

8 Claims, No Drawings

3-(DISUBSTITUTED)AMINOISOTHIAZOLO[3,4-d]PYRIMIDINES

This is a division of application Ser. No. 522,863, filed Nov. 11, 1974 now U.S. Pat. No. 3,959,280.

The present invention relates to novel and useful 3-(disubstituted)aminoisothiazolo[3,4-d]pyrimidines.

The present inventors have succeeded in producing novel 3-(disubstituted)aminoisothiazolo[3,4-d]pyrimidines of the formula

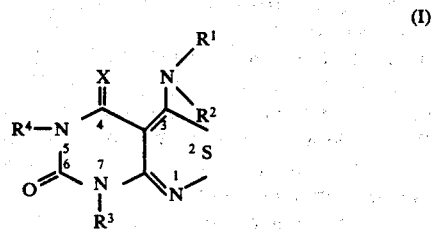

wherein $R^1$, $R^2$ and $R^3$ are respectively alkyl, alkenyl, aryl, aralkyl or aralkenyl, each of which may be substituted, or $R^1$ and $R^2$ form together with the adjacent nitrogen a heterocyclic ring which may be substituted, $R^4$ is hydrogen or alkyl and X is oxygen or imino, with a proviso that when X is imino $R^4$ is hydrogen, and further studies on these compounds have unexpectedly revealed that they show eminent adenosine-3',5'-cyclic phosphate phosphodiesterase-inhibitory activity, and exhibit excellent pharmacological actions such as anti-inflammatory, and sedative actions.

Thus, the principal object of the present invention is to provide the novel compounds (I) which have these excellent pharmacological actions and another object is to provide a pharmaceutical composition comprising one or more of the compounds (I). A further object is to provide a method for the production of the compounds (I) through a novel cyclization reaction. Other objects will be clear from the description and the claims hereinafter.

Referring to the formula (I), the alkyl and alkenyl represented by $R^1$, $R^2$ and $R^3$ may be straight or branched chain and may be advantageously those having up to 5 carbon atoms, which are exemplified by methyl, ethyl, n-propyl, isopropyl, n-butyl, isobutyl, tert-butyl, n-pentyl, n-amyl, 2-butenyl and, methallyl. These lower alkyls and alkenyls may be substituted with hydroxy, halogen (e.g. chlorine, bromine, iodine, fluorine), lower alkoxy (e.g. methoxy, ethoxy, n-propoxy, isopropoxy, n-butoxy, isobutoxy), nitro, lower acyloxy (e.g. formyloxy, acetyloxy). As examples of the substituted lower alkyls, there may be enumerated hydroxymethyl, 2-hydroxyethyl, nitromethyl, α-chloroethyl, β-bromoethyl and α-methoxyethyl. As the aryl designated by $R^1$, $R^2$ and $R^3$, there may be mentioned phenyl and, naphthyl. These aryls may be substituted with lower alkyl (e.g. methyl, ethyl, n-propyl, isopropyl, n-butyl), halogen (e.g. chlorine, bromine, iodine, fluorine), lower alkoxy (e.g. methoxy, ethoxy, n-propoxy, isopropoxy, n-butoxy), nitro. As examples of the substituted aryl, there may be enumerated p-chlorophenyl, p-methylphenyl, p-methoxyphenyl and, p-nitrophenyl. The aralkyl and aralkenyl represented by $R^1$, $R^2$ and $R^3$ may be advantageously those having 7 to 11 carbon atoms which are exemplified by benzyl, phenethyl and, styryl. These aralkyls and aralkenyls may be substituted with lower alkyl (e.g. methyl, ethyl, n-propyl, isopropyl, n-butyl), halogen (e.g. chlorine, bromine, iodine, fluorine), lower alkoxy (e.g. methoxy, ethoxy, n-propoxy, isopropoxy, n-butoxy, isobutoxy), nitro. As examples of the substituted aralkyl, there may be enumerated p-nitrobenzyl, p-chlorobenzyl, p-methylbenzyl and, methoxybenzyl.

As the heterocyclic ring formed by $R^1$ and $R^2$ together with the adjacent nitrogen, the preferred ones are 5- or 6-membered rings, and particularly those containing no hetero-atom except the nitrogen adjacent to $R^1$ and $R^2$ and those containing, in addition to said adjacent nitrogen, another nitrogen or oxygen. These heterocyclic rings may have substituent(s) such as those exemplified in connection with the substituent(s) of the aralkyl and aralkenyl designated by $R^1$, $R^2$ and $R^3$. The additional nitrogen atom in the heterocyclic ring may be substituted by lower acyl. As typical examples of the heterocyclic rings, there may be enumerated piperazine, morpholine, pyrrole, pyrolidine and, 4-formylpiperazine-1-yl.

The alkyl for $R^4$ may be straight or branched chain, and may be advantageously those having up to 5 carbon atoms, which are exemplified by methyl, ethyl, n-propyl, isopropyl and, n-butyl.

The compounds (I) of the present invention can be produced, for example, by reacting a compound of the formula

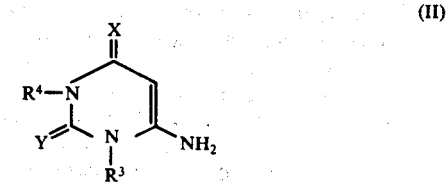

wherein $R^3$, $R^4$ and X have the same meaning as hereinbefore defined and, Y is oxygen or sulfur, with a compound of the formula

wherein $R^1$ and $R^2$ have the same meaning as hereinbefore defined, and a thionyl halide.

The starting compounds (II) are known compounds as a whole and can be easily prepared by procedures which are known per se, for example, by the procedures described in Journal of Organic Chemistry 17, 1879–1890 (1952), Chemische Berichte 96, 2950–2963 (1963), Journal of Organic Chemistry 20, 829–837(1955) and other literatures. Furthermore, 1-substituted-6-aminocytosine falling within the formula (II) can be prepared, for example, by reacting a 1-substituted-6-aminouracil with a phosphorus sulfide compound in the presence of an organic solvent (e.g. pyridine or picoline), reacting the resulting 1-substituted-6-amino-4-thiouracil with an alkyl halide in a solvent (e.g. aqueous alcohol or dimethylformamide), and reacting the resulting 1-substituted-6-amino-4-alkylthiouracil with ammonia in a gas tight reactor, preferably in the presence of a solvent (e.g. alcohol).

The compounds (III) are known compounds as a whole and can be easily prepared by procedures which are known per se, for example by the procedure described in Organic Syntheses, 20, 66 (1940) and, by reacting a corresponding secondary amine, such as diethylamine, diethanolamine, di-n-propanol amine, piperazine, morpholine or the like, with formic acid in an organic solvent (e.g. benzene, toluene) under heating at about 70° to 120° C.

In the compounds (III), when the alkyl and alkenyl designated by $R^1$ and $R^2$ are substituted by lower acyloxy, particularly formyloxy, or when the heterocyclic ring formed by $R^1$ and $R^2$ contains an additional nitrogen is substituted by lower acyl, particularly formyl, the lower acyl in the said lower acyloxy and the lower acyl substituted at the additional nitrogen position respectively function as protective groups as well. These protective lower acyls may be removed, either in the course of the reaction of the present invention or following the reaction, with the aid of an acid or an alkali.

As the compounds (III), there may be mentioned, for example, N,N-dimethylformamide, N,N-diethylformamide, O,O,N-triformyldiethanolamine, O,O,N-triformyldipropanolamine, N,N'-diformylpiperazine, N-formylmorpholine, N-methyl-N-formyl-p-chloroaniline, N-formyl-methylethylamine, N-methyl-N-formylaniline, etc.

Among the thionyl halides which can be employed in the reaction are thionyl chloride, thionyl bromide, etc. Particularly advantageous is thionyl chloride.

In conducting the reaction between the compounds (II), (III) and thionyl halide, it is advantageous to employ, relative to each mole of the compound (II), about 0.5 to 2 moles, preferably about 1 to 1.2 moles of the compound (III), and about 5 to 30 moles, preferably about 15 to 20 moles of thionyl halide.

This reaction is usually conducted in a suitable organic solvent such as dichloromethane, chloroform, benzene, 1,2-dichloroethane or the like. The preferred reaction temperature is about 40° to 150° C.

These compound (II), (III) and thionyl halide may be added all at once or, alternatively, any two of them may be added in the first place and then the remaining one was added thereto.

It is particularly advantageous to add the compound (III) and a thionyl halide in the first place and, then to add the compound (II).

The cyclization among a 6-aminopyrimidine, an N-formyl secondary amine and a thionyl halide was not known, and therefore, the reaction of the present invention is a per se novel cyclization reaction.

In the case where $R^4$ is hydrogen, the compounds (I) may form tautomers shown by the formula

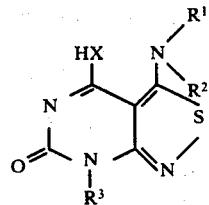

(I')

wherein $R^1$, $R^2$, $R^3$ and X have the same meaning as hereinbefore defined, and these tautomers are also included in the object compounds (I).

The object compounds (I) can be isolated by procedures known per se, for example, concentration to dryness and chromatography. Alternatively, after thionyl halide and acid substances originated from thionyl halide are removed from the reaction mixture, the compounds (I) are isolated by procedures known per se, for example, concentration, extraction, chromatography, recrystallization. The removal of thionyl halide and the acid substances is conducted by known procedures, for example by the following procedure.

The reaction mixture is first poured directly into ice-water. Alternatively, the reaction mixture is concentrated to dryness under reduced pressure and a solution of the concentration residue in water-immiscible solvent (e.g. chloroform, ether, benzene, ethyl acetate) is poured into ice-water. The water layer is neutralized with alkali (e.g. sodium hydrogen carbonate).

Some of the compounds (I), for example the compounds in which the heterocyclic ring formed by $R^1$ and $R^2$ include a nitrogen in addition to the adjacent nitrogen can be easily converted to acid addition salts, particularly mineral acid salts (e.g. hydrochlorides) by procedures which are known per se.

The compounds (I) show eminent adenosine-3',5'-cyclic phosphate phosphodiesterase-inhibitory activity and have excellent pharmacological actions such as anti-inflammatory, and sedative activities.

Among such compounds (I) advantageous are those wherein X is oxygen and particularly each of $R^1$, $R^2$, $R^3$ and $R^4$ is lower alkyl, especially each of $R^1$ and $R^2$ is methyl and each of $R^3$ and $R^4$ is ethyl.

The compounds (I) can each be administered to mammals, including human beings, either as it is or in admixture with a suitable vehicle, orally or parenterally in such optional dosage forms as powders, granules, tablets, injections, etc.

Pharmaceutical compositions containing one or more of the compounds (I) can be prepared by conventional procedures for the preparation of powders, granules, tablets, injections etc. The choice of vehicles may be determined depending upon the route of administration, the solubility of the compounds (I), and so on.

The dosage depends upon such factors as the particular type of compound (I), the symptoms to be dealt with, etc. By way of example, the advantageous daily dose is about 50 to 100 mg. for treatment of anxiety neurosis and about 100 to 200 mg. for treatment of rheumatic fever when orally administed to an adult human.

The following Examples are further illustrative of this invention. It should, of course, be understood that the scope of the invention is by no means limited by or to these examples.

Throughout the foregoing description as well as in the following Examples and Claims, "° C", "N" and "mg.", respectively denote "degrees centigrade", "Normal(s)" and "milligram(s)". The word "part(s)" is based on weight unless otherwise noted and the relationship between "part(s)" and "volume part(s)" corresponds to that between "gram(s)" and "milliliter(s)".

EXAMPLE 1

In 50 parts by volume of 1,2-dichloroethane was dissolved 0.955 part of N,N-dimethylformamide and 25 parts by volume of thionyl chloride was added at 0° C. After 15 minutes, 2.38 parts of 1,3-diethyl-6-aminouracil was added at 0° C and the mixture was stirred at room temperature for 30 minutes and, then, refluxed for 5.5 hours. The reaction mixture was concentrated to dryness under reduced pressure and the residue was dissolved in 200 parts by volume of chloroform. The solution was poured in 150 parts by volume of ice-water. After the water layer was neutralized with sodium hydrogen carbonate, the chloroform layer was taken and washed four times with 100 parts by volume portions of water. The chloroform was distilled off under reduced pressure and the resulting brown-colored syrup was applied to a column of 200 parts of silica gel which was then eluted with chloroform. The fractions rich in the desired product were pooled and concentrated to dryness under reduced pressure.

The concentration residue was recrystallized from methanol. The described procedure yielded 1.5 parts of 3-dimethylamino-5,7-diethyl-isothiazolo(3,4-d)pyrimidine-4,6-(5H, 7H)-dione as colorless needles melting at 88°–90° C. Ultraviolet absorption spectrum $\lambda_{max}^{methanol}$: 235, 278, 308 m$\mu$.

Elemental analysis: Calculated for $C_{11}H_{16}N_4O_2S$ (%) — C, 49.23; H, 6.01; N, 20.88; S, 11.95. Found (%) — C, 49.24; H, 5.89; N, 20.91; S, 11.73.

EXAMPLE 2

In 100 parts by volume of benzene were dissolved 128 parts of 99 % formic acid and 40 parts of diethanolamine and the solution was refluxed in a setup fitted with a water separator.

The mixed-distillate of water and formic acid was discarded.

After about 10 hours of refluxing, the benzene was distilled off under reduced pressure and the residue was distilled under reduced pressure. The procedure yielded 61.5 parts of O,O,N-triformyldiethanolamine as a colorless oil boiling at 155°–160° C (4mmHg.).

In 50 parts by volume of 1,2-dichloroethane was dissolved 2.66 parts of the O,O,N-triformyldiethanolamine and 25 parts by volume of thionyl chloride was added at 0° C. After 15 minutes, 2.52 parts of 1,3-diethyl-6-aminouracil was added at 0° C and the resulting mixture was stirred at room temperature for 30 minutes, after which it was refluxed for 5.5 hours.

After cooling, the reaction mixture was poured in 300 parts by volume of ice-water. The mixture was stirred for a short while and the water layer was neutralized with sodium hydrogen carbonate. The water layer was extracted four times with 50 parts by volume portions of chloroform and the extracts were pooled with the organic layer.

The combined solution was washed three times with 100 parts by volume portions of water and, then, concentrated to dryness under reduced pressure.

The concentration residue was applied to a column of 100 parts silica gel which was then eluted with chloroform-methanol (40:1, V/V). The fractions rich in the desired product were pooled, and concentrated to dryness under reduced pressure.

The residue was recrystallized from ethanol-ether. The described procedure yielded 1.6 parts of 3-[bis-($\beta$-hydroxyethyl)]amino-5,7-diethyl-isothiazolo[3,4-d]pyrimidine-4,6(5H, 7H)-dione as colorless prisms melting at 85°–87° C. Ultraviolet absorption spectrum $\lambda_{max}^{methanol}$: 239, 280, 314 m$\mu$.

Elemental analysis: Calculated for $C_{13}H_{20}N_4O_4S$ (%) — C, 47.54; H, 6.14; N, 17.06; S, 9.77. Found — C, 47.48; H, 6.19; N, 16.97; S, 9.76.

EXAMPLE 3

In 150 parts by volume of benzene were dissolved 170 parts by volume of 99% formic acid and 50 parts by volume of morpholine and, in a manner similar to that described in Example 2, the solution was refluxed and distilled under reduced pressure.

This procedure yielded 56 parts of N-formylmorpholine as a colorless oil boiling at 86°–89° C(4mm Hg.).

In 50 parts by volume of 1,2-dichloroethane was dissolved 2.08 parts of N-formylmorpholine and 30 parts by volume of thionyl chloride was added at 0° C.

After 15 minutes, 2.7 parts of 1,3-diethyl-6-aminouracil was added at 0° C. The mixture was stirred at room temperature for 30 minutes, after which it was refluxed for 5.5 hours. In a manner similar to that described in Example 2, the reaction mixture was extracted, chromatographed and recrystallized from methanol. The procedure yielded 1.9 parts of 3-(morpholin-1-yl)-5,7-diethyl-isothiazolo[3,4-d]pyrimidine-4,6(5H, 7H)-dione as colorless needles melting at 128°–130° C.

Ultraviolet absorption spectrum $\lambda_{max}^{methanol}$: 233, 284, 312 m$\mu$.

Elemental analysis: Calculated for $C_{13}H_{18}N_4O_3S$ (%) — C, 50.30; H, 5.84; N, 18.05; S, 10.33. Found — C, 50.31; H, 5.79; N, 18.28; S, 10.63.

EXAMPLE 4

In 100 parts by volume of chloroform was dissolved 1.5 part of N,N-dimethylformamide and 40 parts by volume of thionyl chloride was added at 0° C. After 15 minutes, 5 parts of 1-ethyl-6-aminouracil was added at 0° C, and the mixture was refluxed for 20 hours. In a manner similar to that described in Example 2, the reaction mixture was extracted, fractionally separated and recrystallized from ethanol. The described procedure yielded 1.6 parts of 3-dimethylamino-7-ethyl-isothiazolo[3,4-d]pyrimidine-4,6(5H, 7H)-dione as colorless needles melting at 222°–223° C.

Ultraviolet absorption spectrum $\lambda_{max}^{ethanol}$: 233, 276, 305 m$\mu$; $\lambda_{max}^{pH11}$: 283 m$\mu$.

Elemental analysis: Calculated for $C_9H_{12}N_4O_2S$ — C, 44.99; H, 5.03; N, 23.32; S, 13.34. Found — C, 44.67; H, 4.68; N, 23.23; S, 13.13.

EXAMPLE 5

In 33 parts by volume of dichloroethane was dissolved 0.75 part of N,N-dimethylformamide and 16 parts by volume of thionyl chloride was added at 0° C. After 15 minutes, 1.8 parts of 1,3-diethyl-6-amino-2-thiouracil was added at 0° C and the mixture was refluxed for 3.5 hours. In a manner similar to that described in Example 2 the reaction mixture was extracted, chromatographed and recrystallized from 10 parts by volume of petroleum ether.

The described procedure yielded 1.1 parts of 3-dimethylamino-5,7-diethyl-isothiazolo[3,4-d]pyrimidine-4,6(5H, 7H)-dione as pale-yellowish needles melting at 88°–89° C Ultraviolet absorption spectrum $\lambda_{max}^{ethanol}$: 235, 278, 307 m$\mu$.

Elemental analysis: Calculated for $C_{11}H_{16}N_4O_2S$ (%) — C, 49.23; H, 6.01; N, 20.88; S, 11.95. Found (%) C, 49.35; H, 6.15; N, 20.48; S, 12.09.

EXAMPLE 6

In 45 parts by volume of dichloroethane was dissolved 1.19 part of N,N-dimethylformamide and 20 parts by volume of thionyl chloride was added at 0° C. After 15 minutes, 2.9 g. of 1-isobutyl-6-aminouracil was added and the mixture was refluxed for 5.5 hours.

In a manner similar to that described in Example 1, the reaction mixture was extracted, chromatographed and recrystallized from 120 parts by volume of methanol. The described procedure yielded 1.8 parts of 3-dimethylamino-7-isobutyl-isothiazolo[3,4-d]pyrimidine-4,6(5H, 7H)-dione as colorless needles melting at 199°-200° C.

Ultraviolet absorption spectrum $\lambda_{max}^{methanol}$: 233, 277, 306 mμ.

Elemental analysis: Calculated for $C_{11}H_{16}N_4O_2S$ (%) — C, 49.23; H, 6.01; N, 20.88; S, 11.95. Found (%) — C, 49.24; H, 6.05; N, 21.06; S, 11.88.

EXAMPLE 7

In 100 parts by volume of benzene were dissolved 200 parts by volume of 85% formic acid and 50 parts of piperazine hexahydrate, and the solution was refluxed in a setup fitted with a water separator.

The mixed-distillate of water and formic acid was discarded.

After about 11 hours of refluxing, the solvent was distilled off under reduced pressure, whereupon a crystalline residue was obtained.

The residue was recrystallized from a mixture of 100 parts by volume of benzene and 100 parts by volume of hexane. The procedure yielded 28 parts of N,N'-diformylpiperazine as colorless prisms melting at 128° C.

In 30 parts by volume of dichloroethane was dissolved 1.56 parts of N,N'-diformylpiperazine and 17 parts by volume of thionyl chloride was added at 0° C. After 15 minutes, 2.39 parts of 1,3-di-n-butyl-6-aminouracil was added, followed by refluxing for 5 hours. In a manner similar to that described in Example 1, the reaction mixture was extracted, chromatographed and recrystallized from 10 parts by volume of ethanol. The procedure yielded 0.6 part of 3-(4-formylpiperazin-1-yl)-5,7-di-n-butyl-isothiazolo[3,4-d]pyrimidine-4,6(5H, 7H)-dione as pale-yellowish needles melting at 195°-205° C.

Ultraviolet absorption spectrum $\lambda_{max}^{ethanol}$: 215, 282, 316 mμ.

Elemental analysis: Calculated for $C_{18}H_{27}N_5O_3S$ (%) — C, 54.95; H, 6.92; N, 17.78; S, 8.15. Found (%) — C, 55.37; H, 6.76; N, 17.02; S, 8.52.

EXAMPLE 8

In 30 parts by volume of dichloroethane was dissolved 1.46 part of N,N'-dimethylformamide and 19 parts by volume of thionyl chloride was added at 0° C. After 15 minutes, 1.71 parts of 1-(2-hydroxyethyl)-6-aminouracil was added at 0° C and the mixture was refluxed for 5.5 hours. The reaction mixture was concentrated to dryness under reduced pressure. To the concentration residue were added 200 parts by volume of chloroform and 200 parts by volume of water and, after the water layer was neutralized with sodium hydrogen carbonate, the mixture was mixed well. The chloroform layer was concentrated to dryness under reduced pressure and the residue was washed twice with 10 parts by volume portions of methanol. The insolubles were recrystallized from 100 parts by volume of chloroform. The described procedure yielded 0.4 part of 3-dimethylamino-7-(2-chloroethyl)-isothiazolo[3,4-d]pyrimidine-4,6(5H, 7H)-dione as colorless needles melting at 255°-262° C (decomp.).

Ultraviolet absorption spectrum: λmax/methanol: 237, 275, 306 mμ; $\lambda_{max}^{OH-}$ 281, 304 mμ.

Elemental anaylsis: Calculated for $C_9H_{11}N_4O_2ClS$ (%) — C, 39.36; H, 4.04; N, 20.36; Cl, 12.90; S, 11.66. Found (%) — C, 39.14; H, 3.94; N, 20.51; Cl, 13.46; S, 11.36.

EXAMPLE 9

In 700 parts by volume of hot pyridine was dissolved 38 parts of phosphorous pentasulfide, followed by the addition of 1 part by volume of water and 20 parts of 1-benzyl-6-aminouracil. The mixture was stirred under heating at 125°-130° C for 5 hours. Then, the reaction mixture was concentrated to about 100 parts by volume and the concentrate poured in 600 parts by volume of ice-water. With stirring, the solution was neutralized with potassium carbonate. It was then allowed to stand in the cold overnight, whereupon 10.5 parts of 1-benzyl-6-amino-4-thiouracil was obtained as a brown-colored powder.

Ultraviolet absorption spectrum: λmax/methanol: 247, 327 mμ; $\lambda_{max}^{OH-}$ 271, 315 mμ.

The above powder of 1-benzyl-6-amino-4-thiouracil (10.5 parts) was suspended in 500 parts by volume of 50% methanol. To this suspension was added 70 parts by volume of a 1N aqueous solution of sodium hydroxide and, then, 3 parts by volume of methyl iodide. The mixture was stirred vigorously at room temperature for 20 minutes. The reaction mixture was neutralized with 1N hydrochloric acid and, then, the methanol was distilled off under reduced pressure. The water layer was chilled to 0° C and the resulting precipitate was recovered by filtration and recrystallized from 250 parts by volume of methanol.

The described procedure yielded 6.7 parts of 1-benzyl-6-amino-4-methylthiouracil as light-purplish flakes melting at 232°-233° C (decomp.).

Ultraviolet absorption spectrum: λmax/methanol: 232, 253, 304 mμ.

Elemental analysis: Calculated for $C_{12}H_{13}N_3OS$ (%) — C, 58.28; H, 5.30; N, 16.99; S, 12.97. Found (%) — C, 58.67; H, 5.54; N, 17.12; S, 12.56.

To the above 1-benzyl-6-amino-4-methylthiouracil (6.7 parts) was added 130 parts by volume of 20% ammonia-methanol and the mixture was heated at 170°-180° C in a sealed tube for 40 hours. The reaction mixture was concentrated to dryness under reduced pressure and the residue was dissolved in 350 parts by volume of hot methanol. After decolorization with activated carbon, the solution was concentrated to about 50 parts by volume to obtain 3.6 parts of pale-yellowish needles of 1-benzyl-6-aminocytosine which decomposes at 260°-265° C.

Ultraviolet absorption spectrum: λmax/methanol: 276 mμ; λmax/H+ 278 mμ.

Elemental analysis: Calculated for $C_{11}H_{12}N_4O$ (%) — C, 61.09; H, 5.60; N, 25.92. Found (%) — C, 59.71; H, 5.24; N, 25.55.

In 120 parts by volume of dichloroethane was dissolved 1.05 part of N,N-dimethylformamide and 20 parts by volume of thionyl chloride was added at 0° C. After 15 minutes, 3 parts of 1-benzyl-6-aminocytosine was added at 0° C and the mixture was refluxed under stirring for 5.5 hours. In a manner similar to that described in Example 2, the reaction mixture was extracted and chromatographed and the fractions rich in the desired product were pooled and concentrated to dryness. The residue was dissolved in 15 parts by volume of methanol and the solution was allowed to cool to room temperature. The procedure yielded 1.4 parts of 3-dimethylamino-4-amino-7-benzyl-isothiazolo[3,4-d]pyrimidin-6(7H)-one as pale yellowish needles melting at 190°-195° C.

Ultraviolet absorption spectrum: λmax/methanol: 262, 299 mμ; λmax/H+ 296, 339 mμ.

Elemental analysis: Calculated for $C_{14}H_{15}N_5OS$ (%) — C, 55.79; N, 5.02; N, 23.24; S, 10.64. Found (%) — C, 55.25; H, 4.72; N, 22.85; S, 10.23.

EXAMPLE 10

To the mixture of 70 parts by volume of thionyl chloride and 125 parts by volume of dichloromethane was added 3.98 parts of N,N-dimethylformamide at 0° C. After the mixture was stirred at 0° C for 15 minutes, 8.55 parts of 1.3-dimethyl-6-aminouracil was added and then refluxed for 5.5 hours. The reaction mixture was concentrated to dryness under reduced pressure and the residue was dissolved in 200 parts by volume of chloroform. The solution was poured in 300 parts by volume of ice-water. After the water layer was neutralized with sodium hydrogen carbonate, the chloroform layer was taken and washed twice with 200 parts by volume portions of each of water. The chloroform was distilled off under reduced pressure. The concentration residue was recrystallized from 80 parts by volume of methanol. The described procedure yielded 6.3 parts of 3-dimethylamino-5,7-dimethyl-isothiazolo[3,4-d]pyrimidine-4,6(5H, 7H)-dione as colorless needles melting at 150°-152° C.

Ultraviolet absorption spectrum: λmax/ethanol: 234, 277, 307 mμ.

Elemental analysis: Calculated for $C_9H_{12}N_4O_2S$ (%) — C, 45.05; H, 5.04; N, 23.32; S, 13.36. Found (%) — C, 44.89; H, 4.79; N, 23.90; S, 13.66.

EXAMPLE 11

To the mixture of 40 parts by volume of thionyl chloride and 70 parts by volume of dichloromethane was added 2.38 parts of N,N-dimethylformamide at 0° C.

After the mixture was stirred at 0° C for 15 minutes, 5.82 parts of 1-(methoxyethyl)-6aminouracil was added and then refluxed for 5.5 hours.

In a manner similar to that described in Example 10, the reaction mixture was extracted, separated and recrystallized from 50 parts by volume of methanol. The described procedure yielded 4.5 parts of 3-dimethylamino-7-(methoxyethyl)-isothiazolo[3,4-d]pyrimidine-4,6(5H, 7H)-dione as colorless needles melting at 161°-163° C.

Ultraviolet absorption spectrum λmax/ethanol: 234, 277, 306 mμ.

Elemental analysis: Calculated for $C_{10}H_{14}N_4O_3S$ (%) — C, 44.43; H, 5.22; N, 20.73; S, 11.86. Found (%) — C, 44.15; H, 4.80; N, 21.11; S, 11.80.

EXAMPLE 12

To the mixture of 70 parts by volume of thionyl chloride and 125 parts by volume of dichloromethane was added 5.5. parts of N,N-diethylformamide at 0° C. After the mixture was stirred at 0° C for 15 minutes, 10 parts of 1,3-diethyl-6-aminouracil was added and then refluxed for 5.5 hours. After the mixture was extracted in a manner similar to that described in Example 1, the extract was applied to a column of 160 parts of silica gel which was then eluted with chloroform. The fractions rich in the desired product were pooled and concentrated to dryness under reduced pressure.

The concentration residue was recrystallized from 50 parts by volume of hexane.

The described procedure yielded 7.9 parts of 3-diethylamino-5,7-diethyl-isothiazolo[3,4-d]pyrimidine-4,6(5H, 7H)-dione as pale-yellowish needles melting at 75°-76° C.

Ultraviolet absorption spectrum λmax/ethanol: 239, 278, 313 mμ.

Elemental analysis: Calculated for $C_{13}H_{20}N_4O_2S$ (%) — C, 52.7; H, 6.80; N, 18.88; S, 10.82. Found (%) — C, 52.35; H, 6.75; N, 19.12; S, 10.46.

EXAMPLE 13

In a manner similar to that described in Examples 1 to 12, the following compounds can be produced.

3-[N-methyl-N(p-chlorophenyl)]amino-5,7-dimethylisothiazolo[3,4-d]pyrimidine-4,6(5H, 7H)-dione, melting at 150°-151° C 3-[N-methyl-N-ethyl[amino-5-methyl-7-benzyl-isothiazolo[3,4d]pyrimidine-4,6(5H, 7H)-dione, melting at 117° C 3-dimethylamino-5-methyl-7-phenyl-isothiazolo[3,4-d]pyrimidine-4,6(5H, 7H)-dione, melting at 153°-155° C 3-(N-methyl-N-phenyl)amino-5-methyl-7-(2-methoxyethyl)isothiazolo[3,4-d]pyrimidine-4,6(5H, 7H)-dione, melting at 122° C 3-diethylamino-5-ethyl-7-(p-chlorophenyl)-isothiazolo[3,4-d]pyrimidine-4,6(5H, 7H)-dione, melting at 127°-128° C

Example 14

An example of practical recipe in which the 3-(disubstituted)aminoisothiazolo[3,4-d]pyrimidines of this invention are utilized as anti-inflammatory agent is as follows:

| Tablet | |
|---|---|
| (1) 3-(dimethylamino)-5,7-diethyl-isothiazolo-(3,4-d)pyrimidine-4,6(5H,7H)-dione | 100.0 mg. |
| (2) lactose | 54.5 mg. |
| (3) corn starch | 35.0 mg. |
| (4) hydroxypropylcellulose | 4.9 mg. |
| (5) magnesium stearate | 0.6 mg. |
| | 195.0 mg. per tablet |

100.0 Parts of (1), 54.5 parts of (2) and 23.5 parts of (3) are throughly mixed, and then the mixture is kneaded in a kneading solution [4.9 parts of (4) in 35 parts by volume of water].

The kneaded mixture is dried and then granulated. 11.5 Parts of (3) and 0.6 parts of (5) are added to the granules and compressed into tablets.

What we claim is:

1. A compound selected from the group consisting of a compound of the formula

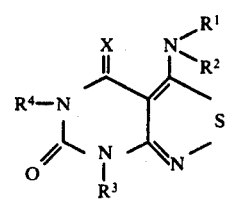

wherein

R¹ and R², together with the adjacent nitrogen atom, form a piperazine, morpholine, pyrrole, pyrrolidine or 4-formylpiperazine-1-yl ring, R³ is selected from the group consisting of (1) alkyl of up to 5 carbon atoms, (2) alkyl of up to 5 carbon atoms, substituted by hydroxy, halogen, lower alkoxy, nitro or lower acyloxy, (3) alkenyl of up to 5 carbon atoms, (4) alkenyl of up to 5 carbon atoms, substituted by hydroxy, halogen, lower alkoxy, nitro or lower acyloxy, (5) phenyl, (6) phenyl substituted by lower alkyl, halogen, lower alkoxy or nitro, (7) naphthyl, (8) naphthyl substituted by lower alkyl, halogen, lower alkoxy or nitro, (9) aralkyl of 7–11 carbon atoms, (10) aralkyl of 7–11 carbon atoms, substituted by lower alkyl, halogen, lower alkoxy or nitro, (11) aralkenyl of 7–11 carbon atoms and (12) aralkenyl of 7–11 carbon atoms substituted by lower alkyl, halogen, lower alkoxy or nitro, R⁴ is hydrogen or alkyl of up to 5 carbon atoms, and X is oxygen or imino, a pharmaceutically acceptable salt of said compound, a tautomer of said compound, and a pharmaceutically acceptable salt of said tautomer, with the proviso that when X is imino R⁴ is hydrogen.

2. A compound as claimed in claim 1, wherein X is oxygen.

3. A compound as claimed in claim 1, wherein X is imino.

4. A compound as claimed in claim 1 wherein R³ is alkyl of up to 5 carbon atoms.

5. A compound as claimed in claim 1, wherein R⁴ is alkyl of up to 5 carbon atoms.

6. The compound as claimed in claim 1, wherein the compound is 3-(morpholin-1-yl)-5,7-diethyl-isothiazolo[3,4-d]pyrimidine-4,6(5H, 7H)-dione.

7. The compound as claimed in claim 1, wherein the compound is 3-(4-formylpiperazin-1-yl)-5,7-di-n-butyl-isothiazolo[3,4-d]pyrimidine-4,6(5H, 7H)-dione.

8. A method for producing a compound selected from the group consisting of a compound of the formula

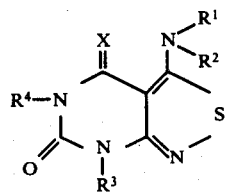

wherein

R¹ and R², together with the adjacent nitrogen atom, form a piperazine, morpholine, pyrrole, pyrrolidine or 4-formylpiperazine-1-yl ring, R³ is selected from the group consisting of (1) alkyl of up to 5 carbon atoms (2) alkyl of up to 5 carbon atoms, substituted by hydroxy, halogen, lower alkoxy, nitro or lower acyloxy, (3) alkenyl of up to 5 carbon atoms, (4) alkenyl of up to 5 carbon atoms, substituted by hydroxy, halogen, lower alkoxy, nitro or lower acyloxy, (5) phenyl, (6) phenyl substituted by lower alkyl, halogen, lower alkoxy or nitro, (7) naphthyl, (8) naphthyl substituted by lower alkyl, halogen, lower alkoxy or nitro, (9) aralkyl of 7–11 carbon atoms, (10) aralkyl of 7–11 carbon atoms, substituted by lower alkyl, halogen, lower alkoxy or nitro, (11) aralkenyl of 7–11 carbon atoms and (12) aralkenyl of 7–11 carbon atoms substituted by lower alkyl, halogen, lower alkoxy or nitro, R⁴ is hydrogen or alkyl of up to 5 carbon atoms, and X is oxygen or imino, a pharmaceutically acceptable salt of said compound, a tautomer of said compound, and a pharmaceutically acceptable salt of said tautomer, with the proviso that when X is imino R⁴ is hydrogen, which method comprises reacting a compound of the formula

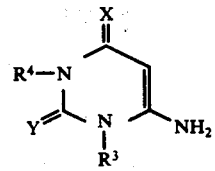

wherein R³, R⁴ and X have the same meanings above and Y is oxygen or sulfur, with a thionyl halide and a compound of the formula

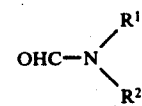

wherein R¹ and R² have the same meanings as above, in an organic solvent at a temperature of about 40° to 150° C.

* * * * *